(12) United States Patent
Sweat

(10) Patent No.: US 7,951,059 B2
(45) Date of Patent: May 31, 2011

(54) BLOOD PROCESSING APPARATUS WITH OPTICAL REFERENCE CONTROL

(75) Inventor: William Sweat, Lakewood, CO (US)

(73) Assignee: CaridianBCT, Inc., Lakewood, CO (US)

( * ) Notice: Subject to any disclaimer, the term of this patent is extended or adjusted under 35 U.S.C. 154(b) by 257 days.

(21) Appl. No.: 12/233,185

(22) Filed: Sep. 18, 2008

(65) Prior Publication Data

US 2010/0065507 A1    Mar. 18, 2010

(51) Int. Cl.
*B04B 15/00* (2006.01)
(52) U.S. Cl. .................................. 494/10; 494/37
(58) Field of Classification Search .............. 494/10, 494/37, 45, 84; 210/91, 745, 782; 700/273
See application file for complete search history.

(56) References Cited

U.S. PATENT DOCUMENTS

| | | | |
|---|---|---|---|
| 4,094,461 A | 6/1978 | Kellogg et al. |
| 4,151,844 A | 5/1979 | Cullis et al. |
| 4,425,112 A | 1/1984 | Ito |
| 4,493,691 A | 1/1985 | Calari |
| 4,557,719 A | 12/1985 | Neuman et al. |
| 4,567,373 A | 1/1986 | O'Meara et al. |
| 4,647,279 A | 3/1987 | Mulzet et al. |
| 4,670,002 A | 6/1987 | Koreeda et al. |
| 4,671,102 A | 6/1987 | Vinegar et al. |
| 4,724,317 A | 2/1988 | Brown et al. |
| 4,834,890 A | 5/1989 | Brown et al. |
| 5,076,911 A | 12/1991 | Brown et al. |
| 5,104,526 A | 4/1992 | Brown et al. |
| 5,159,268 A | 10/1992 | Wu |
| 5,260,598 A | 11/1993 | Brass et al. |
| 5,316,667 A | 5/1994 | Brown et al. |
| 5,322,620 A | 6/1994 | Brown et al. |
| 5,653,887 A | 8/1997 | Wahl et al. |

(Continued)

FOREIGN PATENT DOCUMENTS

DE    3413065    10/1984

(Continued)

OTHER PUBLICATIONS

Salgaller, Michael L., "A Manifesto on the Current State of Dendric Cells in Adoptive Immunotherapy", *Transfusion*, 2003, 43(4):422-424.

(Continued)

*Primary Examiner* — Walter D Griffin
*Assistant Examiner* — Timothy Cleveland
(74) *Attorney, Agent, or Firm* — John R. Merkling; Edna M. O'Connor; Laura B. Arciniegas

(57) ABSTRACT

A density centrifuge blood processing system with automatic two-dimensional optical control of fluid separation by observing fluid characteristics in observation regions. The location of the regions is determined by monitoring an optical reference. Points representing edges of an optical reference are measured and lines are computed through the points. An error measurement is calculated for each line. If the error is too large, the image is abandoned. One of the lines is selected as a referent line. A new line is calculated orthogonal to the referent line. The error function is again computed for the dependant line. If the error exceeds a selected maximum, the frame is discarded. A transformation function translates data points from an (r, s) domain derived from measurements of the edges into an (x, y) domain used to identify pixels in the observation areas.

18 Claims, 13 Drawing Sheets

U.S. PATENT DOCUMENTS

| | | |
|---|---|---|
| 5,722,926 A | 3/1998 | Hlavinka et al. |
| 5,734,464 A | 3/1998 | Gibbs |
| 5,814,279 A | 9/1998 | Biesel et al. |
| 5,889,584 A | 3/1999 | Wardlaw |
| 5,930,033 A | 7/1999 | Inove et al. |
| 5,936,714 A | 8/1999 | Gibbs |
| 5,948,271 A | 9/1999 | Wardwell et al. |
| 5,951,877 A | 9/1999 | Langley et al. |
| 6,006,119 A | 12/1999 | Soller et al. |
| 6,053,856 A | 4/2000 | Hlavinka |
| 6,071,422 A | 6/2000 | Hlavinka et al. |
| 6,254,784 B1 | 7/2001 | Nayk et al. |
| 6,334,842 B1 | 1/2002 | Hlavinka et al. |
| 6,338,820 B1 | 1/2002 | Hubbard et al. |
| 6,354,986 B1 | 3/2002 | Hlavinka et al. |
| 6,506,606 B1 | 1/2003 | Winkelman et al. |
| 6,514,189 B1 | 2/2003 | Hlavinka et al. |
| 6,632,399 B1 | 10/2003 | Kellogg et al. |
| 6,790,371 B2 | 9/2004 | Dolecek |
| 7,327,443 B2 | 2/2008 | Scibona et al. |
| 7,355,685 B2 | 4/2008 | Scibona et al. |
| 7,422,693 B2 | 9/2008 | Carter et al. |
| 2002/0147094 A1 | 10/2002 | Dolecek |
| 2002/0196435 A1 | 12/2002 | Cohen et al. |
| 2003/0113930 A1 | 6/2003 | Winkleman et al. |
| 2004/0245189 A1* | 12/2004 | Robinson et al. ............... 494/37 |
| 2005/0051466 A1 | 3/2005 | Carter et al. |
| 2006/0001860 A1 | 1/2006 | Scibona et al. |
| 2007/0102374 A1 | 5/2007 | Kolenbrander |
| 2008/0045394 A1* | 2/2008 | Kolenbrander et al. ........ 494/37 |

FOREIGN PATENT DOCUMENTS

| | | |
|---|---|---|
| DE | 3301113 | 1/1985 |
| EP | 0392475 | 10/1990 |
| EP | 0729790 | 1/1996 |
| JP | 04371245 | 12/1992 |
| WO | WO96/39618 | 12/1996 |

OTHER PUBLICATIONS

Zhou et al, "FPGA Implementation of a New Hybrid Rotor Position Estimation Scheme Based on Three symmetrical Locked Hall Effect position Sensors", Power Electronics and Motion Control Conference, 2004, IPEMC2004, v. 3, pp. 1592-1596.

* cited by examiner

BLOOD PROCESSING APPARATUS WITH OPTICAL REFERENCE CONTROL

FIELD OF THE INVENTION

The present invention relates to an apparatus and method for separating particles or components of a fluid. The invention has particular advantages in connection with separating blood components, such as platelets or white blood cells.

DESCRIPTION OF THE RELATED ART

In the medical field, it is often necessary to separate blood into components. Whole blood consists of various liquid components and particle components. The liquid portion of blood is largely made up of plasma, and the particle components include red blood cells (erythrocytes), white blood cells (leukocytes), and platelets (thrombocytes). While these constituents have similar densities, their average density relationship, in order of decreasing density, is as follows: red blood cells, white blood cells, platelets, and plasma. In addition, the particle components are related according to size, in order of decreasing size, as follows: white blood cells, red blood cells, and platelets.

Typically, donated platelets are separated or harvested from other blood components using a centrifuge. White cells or other selected components may also be harvested. The centrifuge rotates a blood separation vessel to separate components within the vessel or reservoir using centrifugal force. In use, blood enters the separation vessel while it is rotating rapidly and centrifugal force stratifies the blood components, so that particular components may be separately removed. Components are removed through ports arranged within stratified layers of blood components.

White blood cells and platelets in plasma form a medium-density, stratified layer or "buffy coat". Because typical centrifuge collection processes are unable to consistently and satisfactorily separate white blood cells from platelets in the buffy coat, other processes have been added to improve results. One separation process is one known as centrifugal elutriation. In one common form of elutriation, a cell batch is introduced into a flow of liquid elutriation buffer, which carries the cell batch in suspension into a funnel-shaped chamber located on a spinning centrifuge. As additional liquid buffer solution flows through the chamber, the liquid sweeps smaller sized, slower-sedimenting cells toward an elutriation boundary within the chamber, while larger, faster-sedimenting cells migrate to an area of the chamber having the greatest centrifugal force.

When the centrifugal force and force generated by the fluid flow are balanced, the fluid flow is increased to force slower-sedimenting cells from an exit port in the chamber, while faster-sedimenting cells are retained in the chamber. If fluid flow through the chamber is increased, progressively larger, faster-sedimenting cells may be removed from the chamber.

The apparatus has a fluid separation chamber having a first frustro-conical segment adjacent a fluid inlet and radially inward therefrom, a second frustro-conical segment immediately adjacent the first frustro-conical segment and radially inward therefrom, the second frustro conical segment having a taper such that particles within the second frustro-conical segment are subjected to substantially equal and opposite centripetal and fluid flow forces. The taper of the second frustro-conical segment is selected based on the expected size of particles, such that at least particles of the average size of expected particles will be subjected to substantially equal and opposite centripetal and fluid forces. The apparatus has at least one pump controlling a rate of fluid flow through the fluid separation chamber, a camera configured to observe fluid flow with respect to the fluid separation chamber, and a controller receiving signals from the camera and controlling the motor and the pump.

For these and other reasons, there is a need to improve control of particle separation and/or separation of components of a fluid.

Additional technology related to this application is disclosed in, for example, U.S. Pat. No. 5,722,926, issued Mar. 3, 1998; U.S. Pat. No. 5,951,877, issued Sep. 14, 1999; U.S. Pat. No. 6,053,856, issued Apr. 25, 2000; U.S. Pat. No. 6,334,842, issued Jan. 1, 2002; U.S. patent application Ser. No. 10/905,353, filed Dec. 29, 2004; U.S. patent application Ser. No. 11/163,969, filed Nov. 4, 2005 and in particular U.S. Pat. No. 7,422,693, filed Jul. 1, 2004.

SUMMARY OF THE INVENTION

The present invention comprises a blood component separation apparatus having a rotor for centrifugally separating blood into phases such as red blood cells, buffy coat, or plasma. A camera monitors a separation chamber and image processing determines the location of boundaries. The apparatus controls the position of the boundaries by adjusting the speed of pumps or the rotor or both.

In the present invention, fluid flow in a blood separation chamber in a centrifugal separation device is selectively controlled by optical sensing of two regions in the separation chamber. Interface position may be controlled by optical sensing of a two-dimensional view of the interface in the separation chamber in an area adjacent an outflow port or ports. Gross adjustments, that is, relatively large changes in the location of the interface or interfaces are best controlled by this observation of the interface. Thus in transient states, such as the initial setup of flow conditions, interface position sensing can be effective. Fluid flow may also be controlled in response to the optical intensity (light or dark) of the fluid in the outflow tube. This optical intensity correlates to presence of certain blood components such as red blood cells. Fine adjustments, that is, relatively small changes in the location of the interface are best controlled by sensing the optical intensity in the outflow tube. Thus in steady state conditions, such as the extraction of a blood component through the outflow tube, outflow intensity sensing is more effective.

In a high-speed centrifuge for separating blood components, imaging of the same locations for observation regions from rotation to rotation presents significant problems, particularly in view of the vibrations with high-speed rotation. The present apparatus controls the interface location by measuring light intensity in the collect port monitoring region in the collect port by detecting the presence or absence of RBC's in the collect port, and by monitoring the interface in the phase boundary or interface monitoring region. In order for the apparatus to control the interface a reference position on the disposable blood processing bag, which is carried on the rotor, must be rapidly and reliably determined. In this invention, this is accomplished by a detection algorithm, which monitors an L-shaped calibration marker or optical reference. An intersection derived from edges of the optical reference is used as an origin. A series of points representing an edge is measured. A set of data points, preferably about five (5), is collected for each edge, and a line is computed through the points. An error measurement is calculated for each line. If the error is too large, the image (an "observation" or "frame") for the current rotation is abandoned. The line with the least error is selected as a referent line. A new or dependant line is calculated for the line with the greater error. The error function is again computed for the dependant line. If the error exceeds a selected maximum, the observation or frame is discarded.

Using the parameters of the lines a transformation function is produced, which translates data points from an observation from an (r, s) co-ordinate domain derived from measurements of the edges into an (x, y) co-ordinate domain used to identify pixels in the observation areas. To test the transformation, the data points for the two edges are translated from the (r, s) domain into the (x, y) domain and the error function is computed once again. If the error exceeds the maximum error limit, the frame is abandoned.

If the data passes the tests, the pixels falling within the observation regions identified with reference to the origin that has been identified as the intersection of the referent and dependant lines are used determine the position of phase boundaries and out flow characteristics. The process outlined above and described more completely hereafter allows for a frame by frame determination of the location of an origin in the pixel field of the camera and for a determination that the image is sufficiently clear for the collection of data. Vibration and relative motion between the rotor and separation chamber and the camera causes the image detected by the camera to move in the (x, y) plane and to come in and out of focus. The method described allows the apparatus to discard a frame or observation that is too blurry to provide accurate data and to locate a consistent origin from frame to frame.

It is an object of the present invention to provide a density centrifuge blood processing system for separating fluid components comprising a separation chamber rotating about a central rotation axis, the separation chamber having an optical reference mounted thereon, and a computational apparatus distinguishing the optical reference and establishing reference co-ordinates for gathering data from at least one observation of the observation region detected by the first detector.

It is also an object of the invention that computational apparatus rejects an observation of the separation chamber if an error measurement of the optical reference is not within a pre-selected error.

A further object of the invention is to translate data from the observation of the observation region from a first co-ordinate domain into a second co-ordinate domain.

Another object is to provide an optical reference comprising at least two non-parallel sides and wherein said computational apparatus recognizes a first side represented by a first line and further fits a second line to a second side according to a known angle between said first side and said second side and to reject an observation of the separation chamber if data representing an edge of the optical reference are not within a pre-selected error.

It is also an object of the invention to compute an error measurement for each of the first and second sides and to select the side with the least error as a referent line, to compute a dependant line for the side with the greater error, to re-compute an error measurement for the dependant line, and to reject an observation of said separation chamber if the error measurement for the dependant line is not within a pre-selected error.

These and other objects and features of the present invention will be apparent from the following detailed description. It is to be understood that both the foregoing general description and the following detailed description are exemplary, and are intended to provide further explanation of the invention as claimed.

DETAILED DESCRIPTION

The present invention preferably comprises a blood processing apparatus having a camera control system, as disclosed in U.S. Pat. No. 7,422,693 and in U.S. application Ser. Nos. 10/905,353 and 11/772,692 and 11/774,073. It may also be practiced with a TRIMA® blood component centrifuge manufactured by CaridianBCT, Inc. of Colorado (formerly Gambro BCT, Inc.) or, alternatively, with a COBE® SPECTRA single-stage blood component centrifuge also manufactured by CaridianBCT, Inc. Both the TRIMA® and the SPECTRA centrifuges incorporate a one-omega/two-omega sealless tubing connection as disclosed in U.S. Pat. No. 4,425,112 to Ito. The SPECTRA centrifuge also uses a single-stage blood component separation channel substantially as disclosed in U.S. Pat. No. 4,094,461 to Kellogg et al. and U.S. Pat. No. 4,647,279 to Mulzet et al. The invention could also be practiced with a TRIMA® or TRIMA ACCEL® centrifugal separation system or other types of centrifugal separator. The method of the invention is described in connection with the aforementioned blood processing apparatus and camera control system for purposes of discussion only, and this is not intended to limit the invention in any sense.

Figure 1:
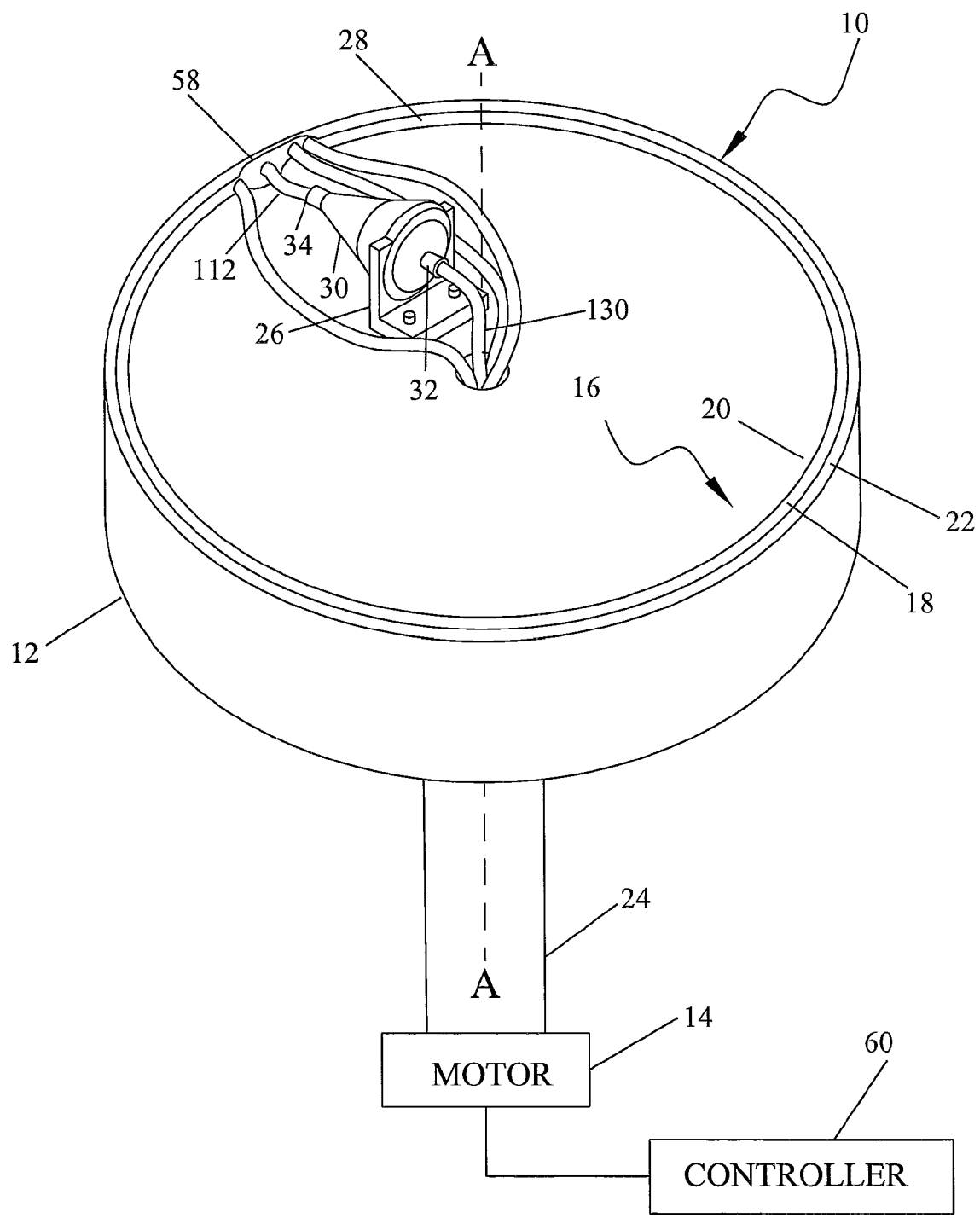
FIG. 1 is a partial perspective, schematic view of a blood processing centrifuge apparatus including a fluid chamber.

As embodied herein and illustrated in FIG. 1, a centrifuge apparatus 10 has a centrifuge rotor 12 coupled to a motor 14 so that the centrifuge rotor 12 rotates about its axis of rotation A-A. The motor 14 is coupled to the rotor 12 directly or indirectly through a shaft 24 connected to the rotor 12. Alternately, the shaft 24 may be coupled to the motor 14 through a gearing transmission (not shown).

Figure 4:
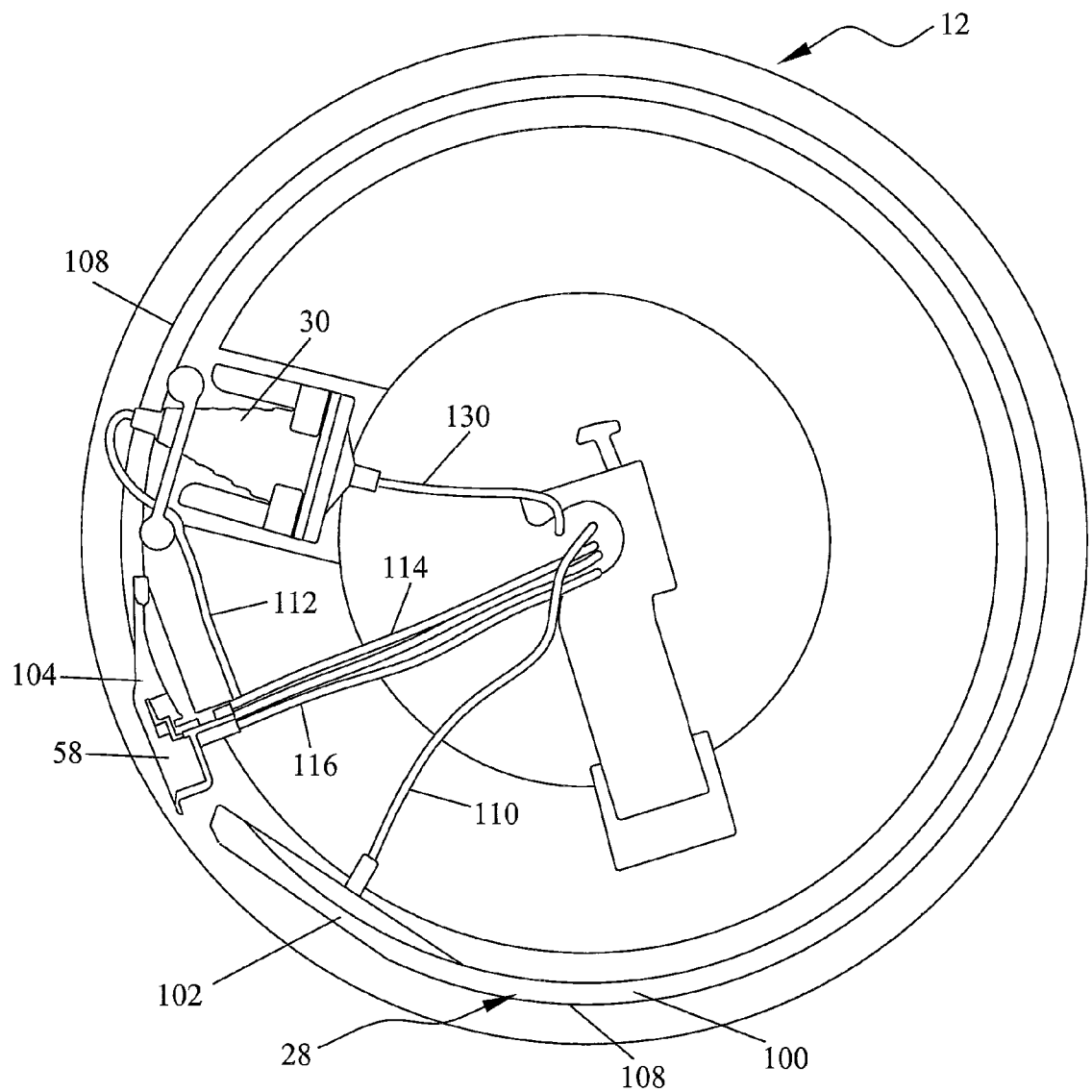
FIG. 4 is a partial cross-sectional, schematic view of a portion of a separation vessel and the fluid chamber mounted on a centrifuge rotor of FIG. 1.

The rotor 12 has a retainer 16 including a passageway or annular groove 18 having an open upper surface adapted to receive a separation vessel 28, shown in pertinent part in FIG. 4. The groove 18 completely surrounds the rotor's axis of rotation A-A and is bounded by an inner wall 20 and an outer wall 22 spaced apart from one another to define the groove 18. Although the groove 18 shown in FIG. 1 completely surrounds the axis of rotation A-A, the groove could partially surround the axis A-A if the separation vessel is not annular. Preferably, a substantial portion of the groove 18 has a constant radius of curvature about the axis of rotation A-A and is positioned at a maximum possible radial distance on the rotor 12. This shape ensures that substances separated in the separation vessel 28 undergo relatively constant centrifugal forces as they pass from an inlet portion to an outlet portion of the separation vessel 28.

As shown in FIG. 1, a bracket 26 is provided on a top surface of the rotor 12. The bracket 26 releasably holds a fluid chamber 30 on the rotor 12 so that an outlet 32 of the fluid chamber 30 is positioned closer to the axis of rotation A-A than an inlet 34 of the fluid chamber 30. The bracket 26 preferably orients the fluid chamber 30 on the rotor 12 with a longitudinal axis of the fluid chamber 30 in a plane transverse to the rotor's axis of rotation A-A. In addition, the bracket 26 is preferably arranged to hold the fluid chamber 30 on the rotor 12 with the fluid chamber outlet 32 facing the axis of rotation A-A. Although the fluid chamber 30 is shown on a top surface of the rotor 12, the fluid chamber 30 could also be secured to the rotor 12 at alternate locations, such as beneath the top surface of the rotor 12.

Figure 2:
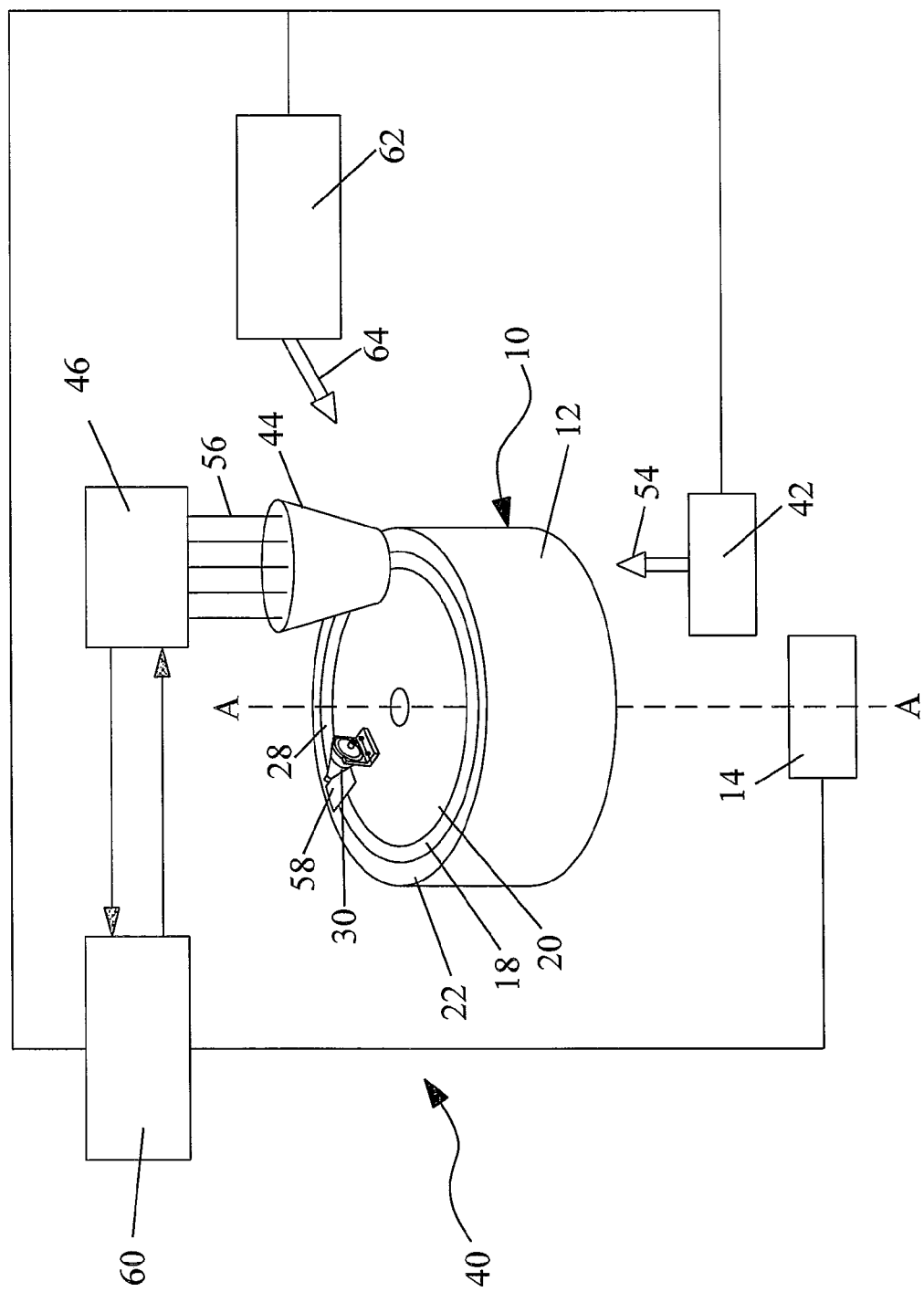
FIG. 2 is a partial perspective, schematic view of the centrifuge apparatus and a control camera.

FIG. 2 schematically illustrates an exemplary embodiment of an optical monitoring system 40 capable of measuring a distribution of scattered and/or transmitted light intensities corresponding to patterns of light originating from an observation region on the separation vessel 28. The monitoring system 40 comprises light source 42, light collection element 44, and detector 46. Light source 42 is in optical communication with the centrifuge apparatus 10 comprising rotor 12, which rotates about central rotation axis A-A. Rotation about central rotation axis A-A results in separation of a blood sample in the separation vessel 28 into discrete blood components.

Light source 42 provides incident light beam 54, which stroboscopically illuminates an observation region 58 when the observation region 58 passes under the light collection element 44. Light source 42 is capable of generating an incident light beam, a portion of which is transmitted through at least one blood component undergoing separation in separation vessel 28. At least a portion of scattered and/or transmitted light 56 from the observation region 58 is collected by light collection element 44. Light collection element 44 is capable of directing at least a portion of the collected light 56 onto detector 46. The detector 46 detects patterns of scattered and/or transmitted light 56 from the observation region. The observation region 58 may also be illuminated by an upper light source 62, which is positioned on the same side of the separation chamber as the light collection element 44 and detector 46. Upper light source 62 is positioned such that it generates an incident beam 64, which is scattered by the blood sample and/or centrifuge. A portion of the light from upper light source 62 is collected by light collection element 44 and detected by detector 46, thereby measuring a distribution of scattered and/or transmitted light intensities.

Distributions of scattered and/or transmitted light intensities comprise images corresponding to patterns of light originating from the observation region 58. The images may be monochrome images, which provide a measurement of the brightness of separated blood components along the separation axis. Alternatively, the images may be color images, which provide a measurement of the colors of separated blood components along the separation axis. Observation region 58 is positioned on a portion of the density centrifuge 10, preferably on the separation vessel 28. The fluid chamber 30 may also be an observation region, as explained below. In the exemplary embodiment illustrated in FIG. 4 and FIG. 5, separated blood components and phase boundaries between optically differentiable blood components are viewable in observation region 58.

Detector 46 is also capable of generating output signals corresponding to the measured distributions of scattered and/or transmitted light intensities and/or images. The detector 46 is operationally connected to a device controller 60 capable of receiving the output signals. Device controller 60 displays the measured intensity distributions, stores the measured intensity distributions, processes measured intensity distributions in real time, transmits control signals to various optical and mechanical components of the monitoring system and centrifuge or any combination of these. Device controller 60 is operationally connected to centrifuge apparatus 10 and is capable of adjusting selected operating conditions of the centrifuge apparatus, such as the flow rates of cellular and non-cellular components out of the separation vessel 28 or fluid chamber 30, the position of one or more phase boundaries, rotational velocity of the rotor about central rotation axis A-A, the infusion of anticoagulation agents or other blood processing agents to the blood sample, or any combination of these.

Device controller 60 can also be operationally connected to light source 42 and/or upper light source 62. Device controller 60 and/or detector 46 are capable of generating output signals for controlling illumination conditions. For example, output signals from the detector 46 can be used to control the timing of illumination pulses, illumination intensities, the distribution of illumination wavelengths and/or position of light source 42 and/or upper light source 62. Device controller 60 and detector 46 are in two-way communication, and the device controller sends control signals to detector 46 to selectively adjust detector exposure time, detector gain and to switch between monochrome and color imaging.

Light sources comprise light emitting diode (LED) sources capable of generating one or more incident beams for illuminating an observation region on the centrifuge. A plurality of lamps may be positioned to illuminate a single side or multiple sides of the centrifuge apparatus 10. Light emitting diodes and arrays of light emitting diode light sources are preferred for some applications because they are capable of generating precisely timed illumination pulses. Preferred light sources generate an incident light beam having a substantially uniform intensity, and a selected wavelength range.

The optical monitoring system comprises a plurality of light sources, each capable of generating an incident light beam having a different wavelength range, for example, a combination of any of the following: white light source, red light source, green light source, blue light source and infra red light source. Use of a combination of light sources having different wavelength ranges is beneficial for discriminating and characterizing separated blood fractions because absorption constants and scattering coefficients of cellular and non-cellular components of blood vary with wavelength. For example, a component containing red blood cells is easily distinguished from platelet-enriched plasma by illumination with light having wavelengths selected over the range of about 500 nm to about 600 nm, because the red blood cell component absorbs light over this wavelength significantly more strongly that the platelet-enriched plasma component. In addition, use of multiple colored light sources provides a means of characterizing the white blood cell type in an extracted blood component. As different white blood cell types have different absorption and scattering cross sections at different wavelengths, monitoring transmitted and/or scattered light from a white cell-containing blood component provides a means of distinguishing the various white blood cell types in a blood component and quantifying the abundance of each cell-type.

The light sources provide a continuous incident light beam or a pulsed incident light beam. Pulsed light sources are switched on and off synchronously with the rotation of the rotor 12 to illuminate an observation region having a substantially fixed position on the rotor 12. Alternatively, pulsed light sources of the present invention can be configured such that they can be switched on and off at different angular positions, synchronous with the rotation of the rotor 12, illuminating different observation regions for each full rotation. This alternative embodiment provides a method of selectively adjusting the location of the observation region and, thereby, probing different regions of the separation chamber 28 or of the fluid chamber 30. Triggering of illumination pulses may be based on the rotational speed of the centrifuge or on the angular position of the separation chamber or the fluid chamber 30 as detected by optical or electronic methods well known in the art. Triggering may be provided by trigger pulses generated by the device controller 60 and/or detector 46.

Figure 3:
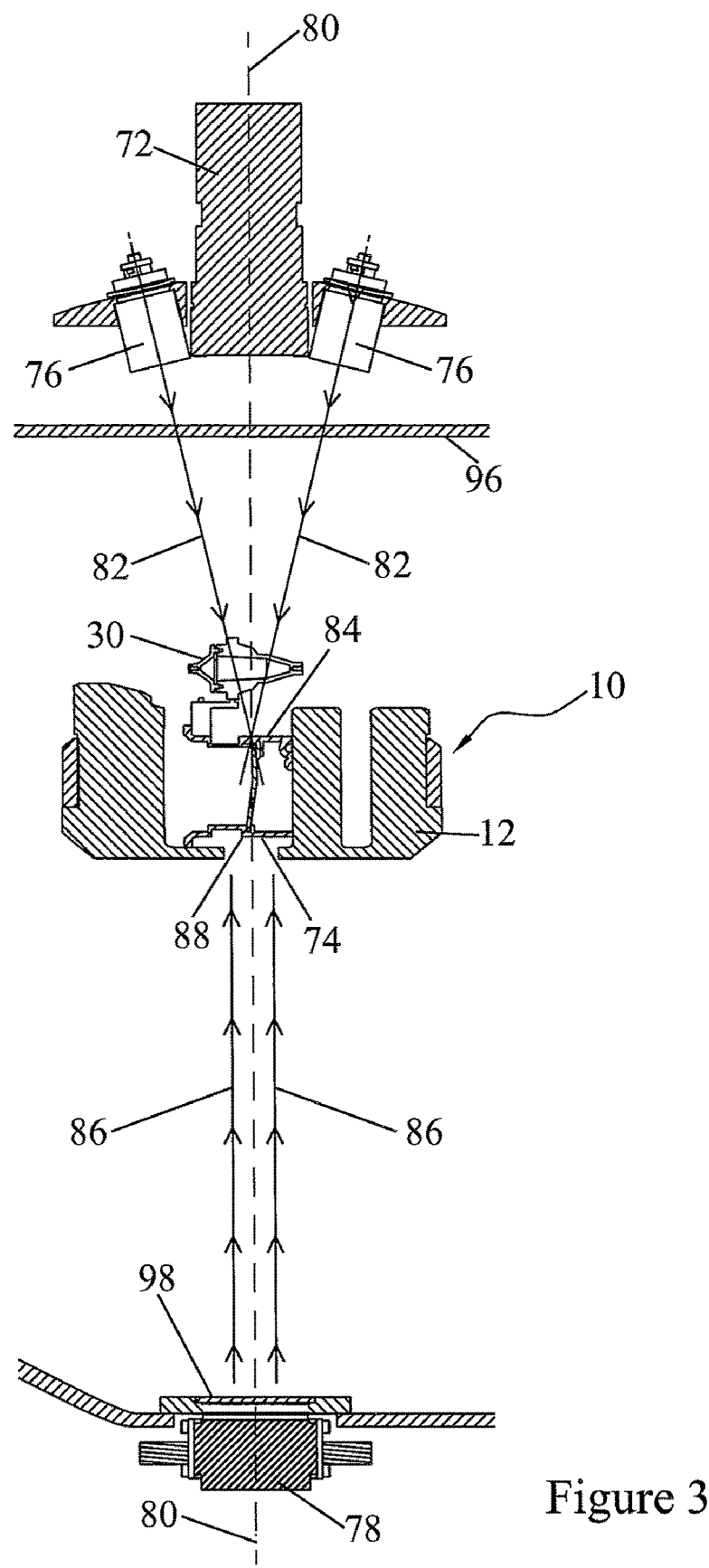
FIG. 3 is a partial cross-sectional view of blood processing apparatus of FIG. 2, including the fluid chamber of FIG. 1.

FIG. 3 is a cutaway view of the optical monitoring system 40. The illustrated optical monitoring system 40 comprises CCD ("charge-coupled device") camera 72 (CMOS ("complementary metal oxide semiconductor") or other cameras could also be used) equipped with a fixed focus lens system (corresponding to the light collection element 44 and detector 46), an optical cell 74 (corresponding to the observation region 58), an upper LED light source 76 (corresponding to the upper light source 62), and a bottom pulsed LED light source 78 (corresponding to the light source 42). As illustrated in FIG. 3, CCD camera 72 is in optical communication with optical cell 74 and positioned to intersect optical axis 80. Upper LED light source 76 is in optical communication with optical cell 74 and is positioned such that it is capable of directing a plurality of collimated upper light beams 82, propagating along propagation axes that intersect optical axis 80, onto the top side 84 of optical cell 74. Bottom pulsed LED light source 78 is also in optical communication with optical cell 74 and is positioned such that it is capable of directing a plurality of collimated bottom light beams 86, propagating along optical axis 80, onto the bottom side 88 of optical cell 74.

CCD camera 72 may be positioned such that the focal plane of the fixed focus lens system is substantially co-planar with selected optical surfaces of optical cell 74, such as optical surfaces corresponding to an interface monitoring region, calibration markers, one or more extraction ports and one or more inlets. The CCD camera 72 is separated from the center of the fixed focus lens system by a distance along optical axis 80 such that an image corresponding to selected optical surfaces of optical cell 74 is provided on the sensing surface of the CCD camera. This optical configuration allows distributions of light intensities comprising images of rotating optical cell 74 or of fluid chamber 30 to be measured and analyzed in real time.

Referring to FIG. 3, first transparent plate 96 is provided between CCD camera 72 and optical cell 74, and second transparent plate 98 is provided between bottom LED light source 78 and optical cell 74. First and second transparent plates 96 and 98 physically isolate CCD camera 72, upper LED light source 76 and bottom LED light source 78 from optical cell 74 so that these components will not contact a sample undergoing processing in the event of sample leakage from the separation chamber 28. In addition, first and second transparent plates 96 and 98 minimize degradation of CCD camera 72, upper LED light source 76 and bottom LED light source 78 due to unwanted deposition of dust and other contaminants that can be introduced to the system upon rotation of the separation chamber and filler. Further, first and second transparent plates 96 and 98 also allow a user to optimize the alignment of the camera 72, upper LED light source 76 and bottom LED light source 78 without exposure to a blood sample in the separation chamber 28. First and second transparent plates 96 and 98 can comprise any material capable of transmitting at least a portion of upper and bottom illumination light beams 82 and 86. Exemplary materials for first and second transparent plates 96 and 98 include, but are not limited to, glasses such as optical-quality, scratch-resistant glass, transparent polymeric materials such as transparent plastics, quartz, or inorganic salts.

FIG. 4 schematically illustrates the separation vessel 28 and fluid chamber 30 mounted on the rotor 12. The separation vessel 28 has a generally annular flow path 100 and includes an inlet portion 102 and outlet portion 104.

A radial outer wall 108 of the separation vessel 28 is positioned closer to the axis of rotation in the inlet portion 102 than in the outlet portion 104. During separation of blood components, this arrangement causes formation of a very thin and rapidly advancing red blood cell bed in the separation vessel 28 between the inlet portion 102 and outlet portion 104. The red blood cell bed substantially limits or prevents platelets from contacting the radial outer wall 108 of the separation vessel 28. This is believed to reduce clumping of platelets caused when platelets contact structural components of centrifugal separation devices.

The inlet portion 102 includes an inflow tube 110 for conveying a fluid to be separated, such as whole blood, into the separation vessel 28. During a separation procedure, substances entering the inlet portion 102 follow the flow path 100 and stratify according to differences in density in response to rotation of the rotor 12. The outlet portion 104 includes first, second, and third outlet lines 112, 114, 116 for removing separated substances from the separation vessel 28. Preferably, each of the components separated in the vessel 28 is collected and removed in only one area of the vessel 28, namely the outlet portion 104. In addition, the separation vessel 28 preferably includes a substantially constant radius except in the region of the outlet portion 104 where the outer wall of the outlet portion 104 is preferably positioned farther away from the axis of rotation to allow for outlet ports of the lines 112, 114, and 116 to be positioned at different radial distances and to create a collection pool with greater depth for the high density red blood cells. The outlet port of line 114 is farther from the axis of rotation A-A than the other ports to remove higher density components, such as red blood cells. The port of line 116 is located closer to the axis of rotation than the other ports to remove the least dense components separated in the separation vessel 28, such as plasma. The first line 112 collects intermediate density components and, optionally, some of the lower density components. The first line 112 may be coupled to the inlet 34 of the elutriation chamber 30. The outlet 32 of the elutriation chamber 30 is coupled to a line 130. The second and third lines 114 and 116 are positioned downstream (not shown) from first line 112 to collect the high and low density components.

The positions of the interfaces are controlled by the CCD camera 72 monitoring the position of the interface and controlling flow of liquid and/or particles in response to the monitored position. Further details concerning the structure and operation of the separation vessel 28 are described in U.S. Pat. No. 7,422,693 and also in U.S. Pat. No. 4,094,461 to Kellogg et al. and U.S. Pat. No. 4,647,279 to Mulzet et al.

Figure 5:
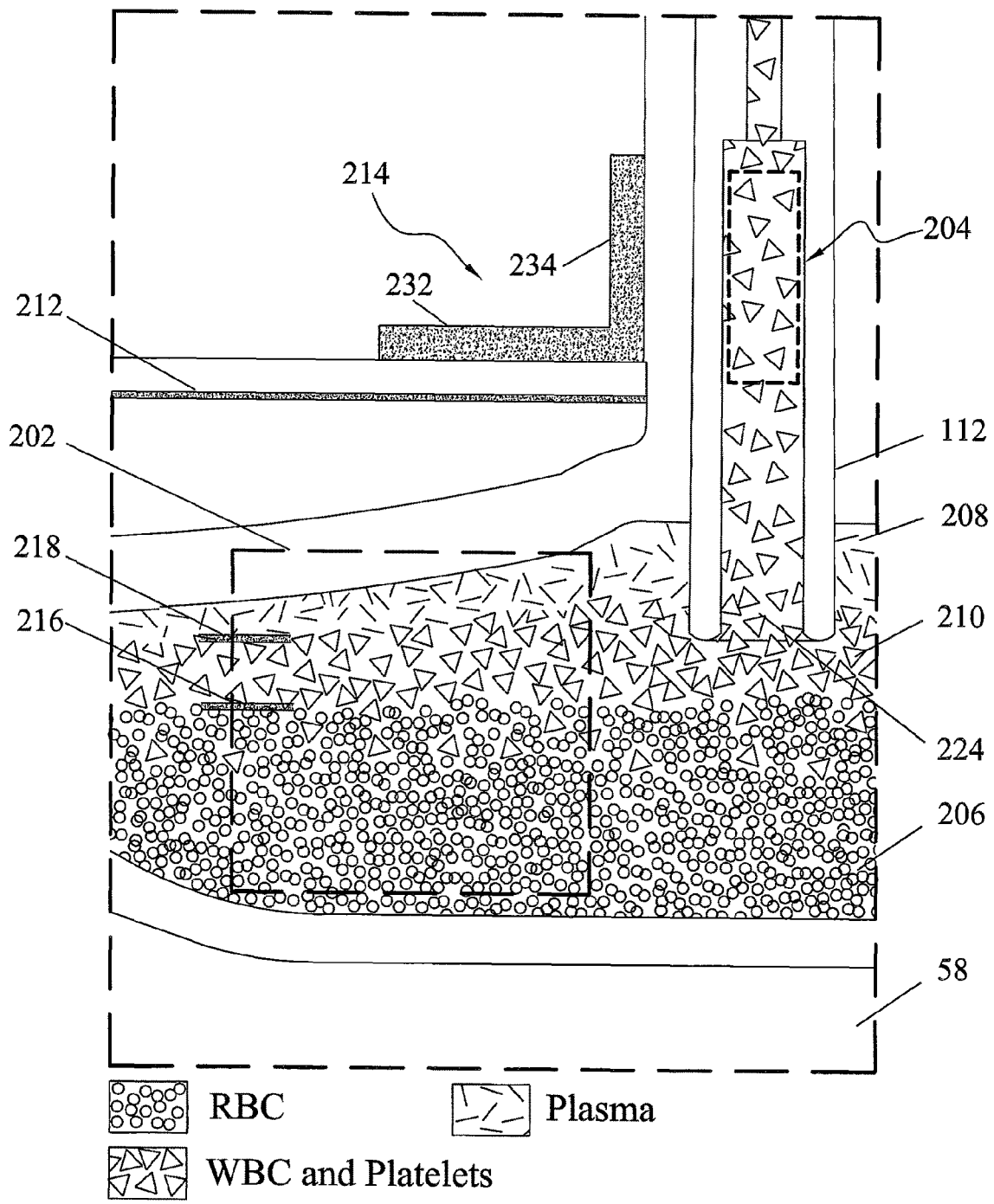
FIG. 5 is a plan view of a separation chamber of the separation vessel of FIG. 4.
Figure 6:
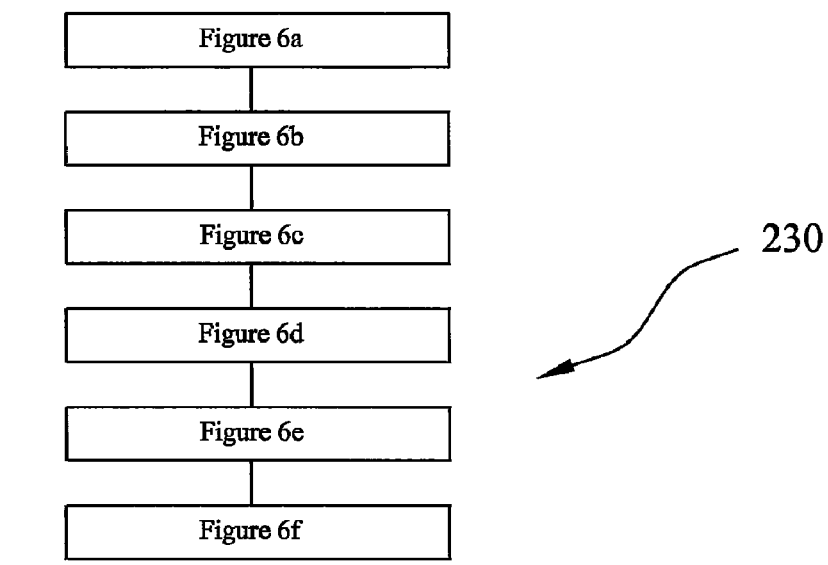
FIG. 6 is a graphic representation of steps for image processing according to the present invention.
Figure 6A:
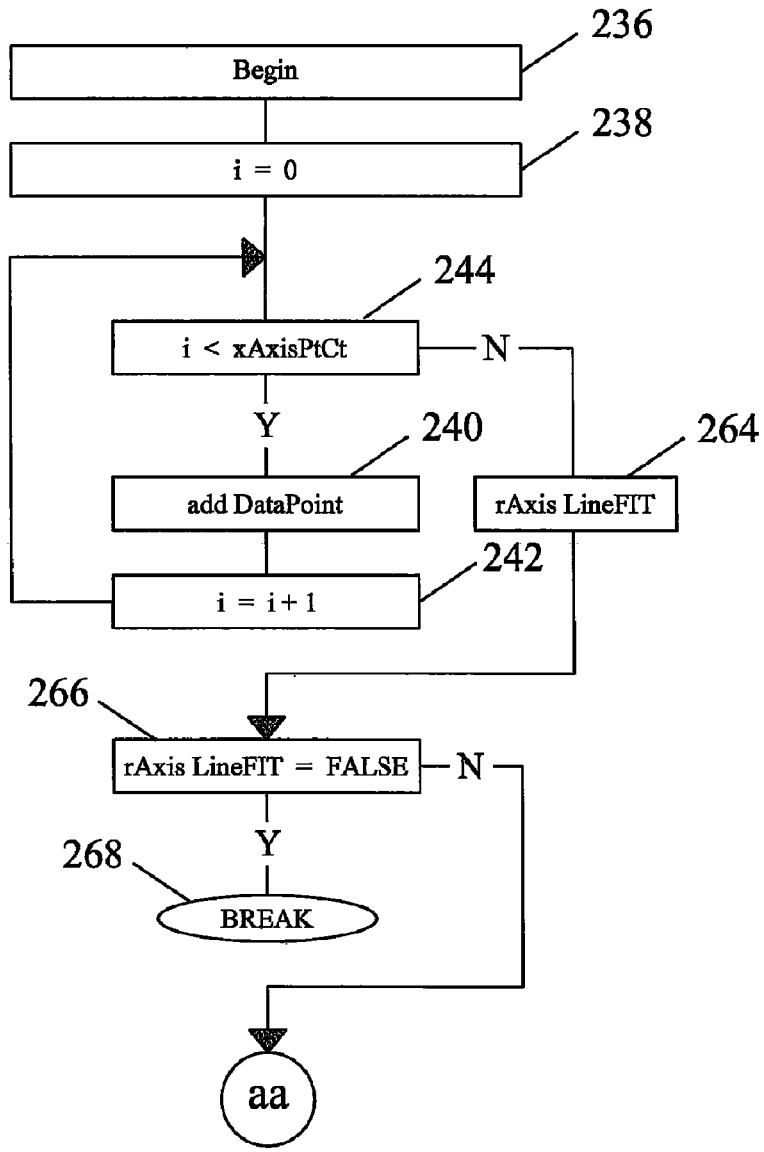
Figure 6B:
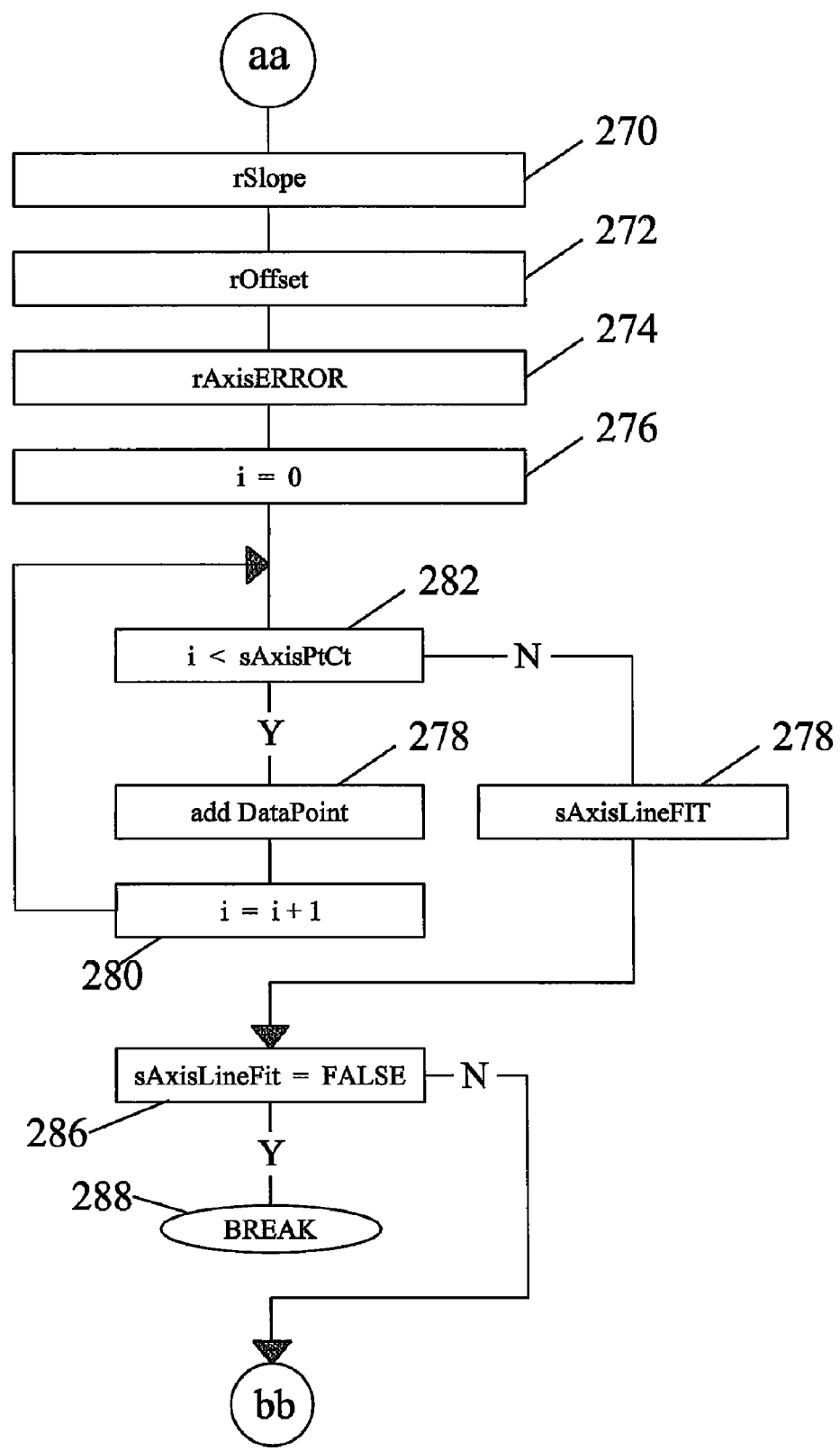
Figure 6C:
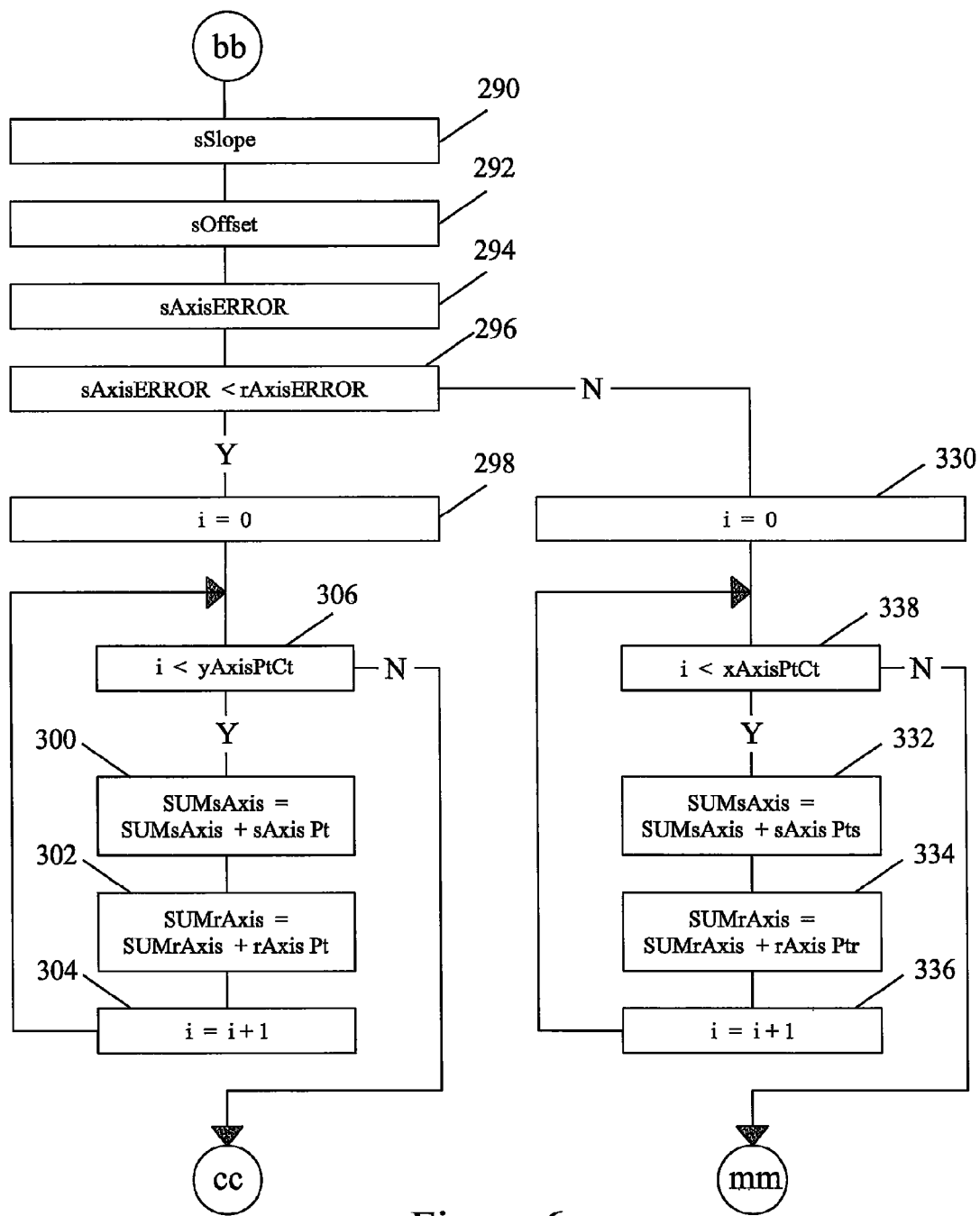
Figure 6D:
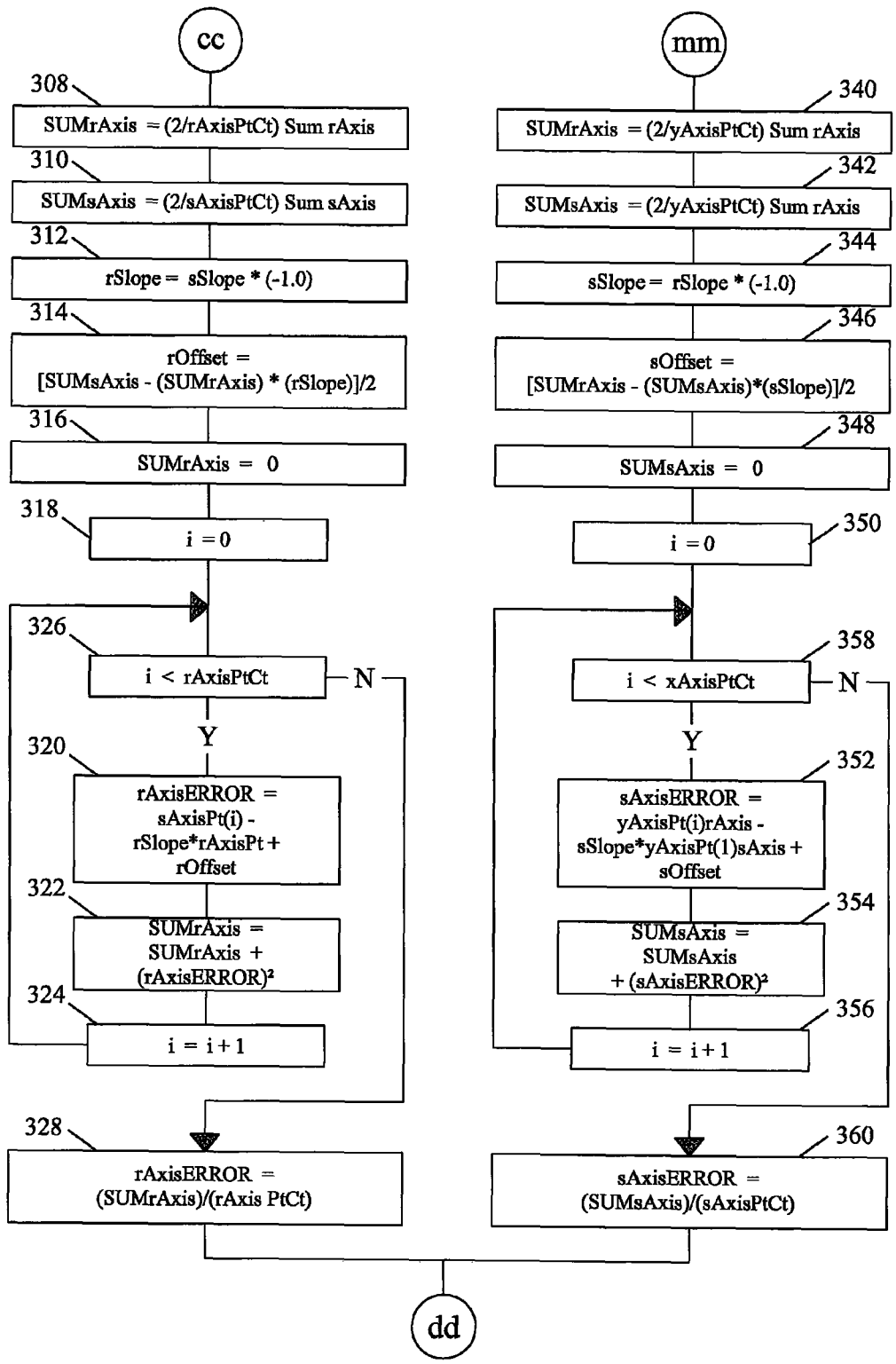
Figure 6E:
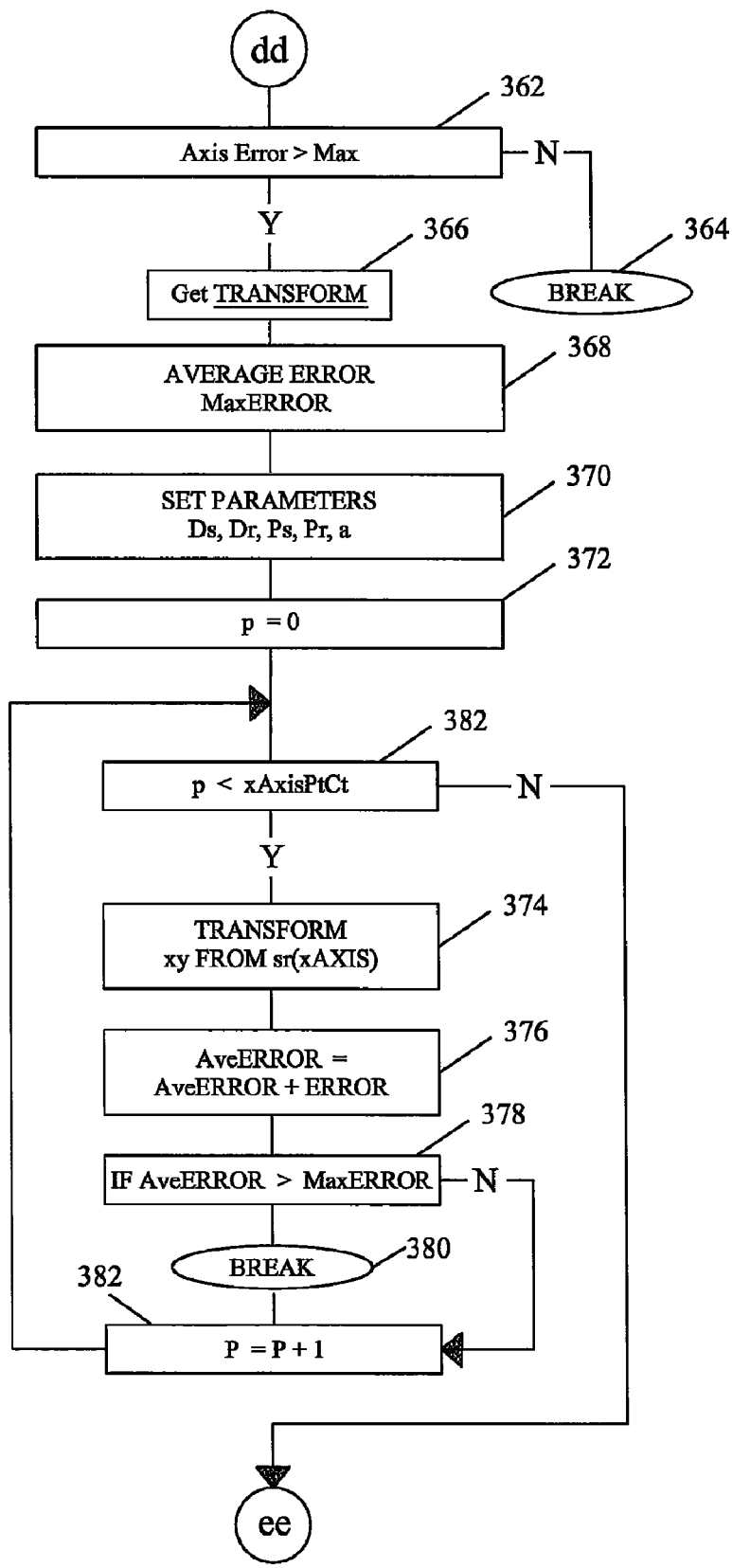
Figure 6F:
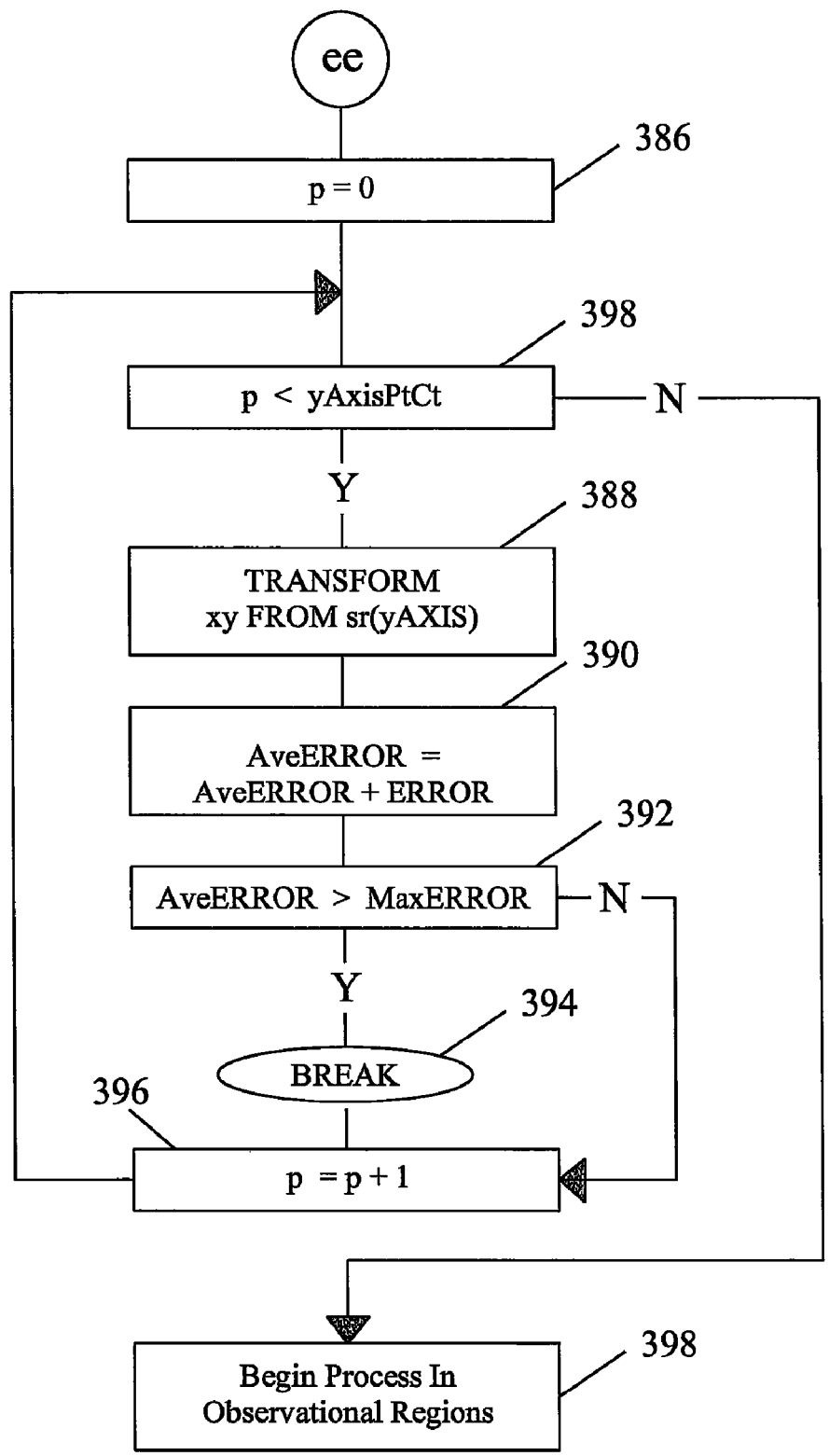

Referring to FIG. 2, the camera 44 is generally focused on the separation vessel 28 and stroboscopic illumination allows an observation region 58 around the first, second, and third lines 112, 114, and 116 to be observed. Using information gathered through the camera, the controller 60 regulates the position of interfaces between various blood components, such as plasma, buffy coat (containing monocytes and/or white blood cells and platelets) and red blood cells by controlling the pumps (not shown) connected to lines 110, 114, 116, and 130. FIG. 5 shows an image of the observation region 58 generated by the methods of U.S. Pat. No. 7,422,693 corresponding to the separation of a human blood sample and extraction of a separated platelet-containing blood component. The observation region 58 shown in FIG. 5 includes a phase boundary monitoring region 202 and an extraction or collect port monitoring region 204. Visible in phase boundary monitoring region 202 are a red blood cell component 206, a plasma component 208 and a mixed-phase buffy coat layer 210, which has both white blood cells and platelets. Calibration markers are also apparent in the image in FIG. 5. Near an edge 212 of the optical cell 74 is an L-shaped calibration marker or optical reference 214 for determining the absolute position of phase boundaries between optically differentiable blood components. Inner edges 232, 234 of the optical reference 214 are used to indicate the positions and physical dimensions of the phase boundary monitoring region 202 and the platelet collect port monitoring region 204. The physical dimension may be determined by adjusting the optics to within a selected range and then configuring the software with a parameter to convert pixels to microns. Alternatively, the thickness of the optical reference, usually about 1 mm, could be used. Light intensities transmitted through the phase boundary monitoring region 202 are acquired as a function of time and analyzed in real time to provide measurements of the position of the phase boundary 216 between red blood cell component 206 and buffy coat layer 210 and the phase boundary 218 between the buffy coat layer 210 and plasma component 208. All boundary layer positions are measured relative to the edge of the optical reference 214.

Collect port monitoring region 204 monitors flow in first line 112 of the optical cell for extracting a blood component, for example, buffy coat. The apparatus responds to changes in detected blood component flow to establish a correct phase boundary level and further responds to changes in observed phase boundaries to maintain a consistent phase boundary level. The system discriminates between a plasma flow condition, a buffy coat flow condition, and a red blood cell flow condition, and can detect pump-induced flow variation in the blood component flow in the collect port measuring area. A plasma signal limit and a red blood cell signal limit may be set and the flow of fluid adjusted based on said limits. The system derives a statistical measure of fluid flow in the collect port measuring area, which may be a moving median of the average value of intensity of pixels in the collect port measuring area.

In this example, first line 112 having orifice 224 is configured to collect buffy coat in the human blood sample and extends a distance along the separation axis such that it terminates proximate to the buffy coat layer in the rotating separation chamber. The two-dimensional distribution of light intensities of light transmitted through the collect port in the collect port monitoring region 204 depends on the concentration, and spatial distribution and cell-type of cellular material exiting the separation chamber. Light intensities transmitted through the collect port monitoring region 204 are acquired as a function of time and analyzed to characterize the composition and flux of cellular material out of the separation chamber 28. As cellular materials, such as white blood cells and red blood cells, absorb and scatter light from the light sources, passage of cellular material through the extraction port decreases the observed light intensities.

The first collection line 112 is connected to the fluid chamber inlet 34 to pass the intermediate density components into the fluid chamber 30. Components initially separated in the separation vessel 28 are further separated in the fluid chamber 30. For example, white blood cells could be separated from plasma and platelets in the fluid chamber 30. This further separation preferably takes place by forming a saturated fluidized bed of particles in the fluid chamber 30. The fluid chamber 30 may be formed of a transparent or translucent co-polyester plastic, such as PETG, to allow viewing of the contents within the chamber interior with the aid of the camera during a separation procedure.

The apparatus 10 includes the controller 60 (FIG. 1) connected to the motor 14 to control rotational speed of the rotor 12. The controller 60 is connected to the pumps in lines 110, 114, 116, and 130 to control the flow rate of substances flowing to and from the separation vessel 28 and the fluid chamber 30. The controller 60 controls the operation and flow rate of the pumps to permit the temporary purging of the fluid chamber 30. The controller 60 may include a computer having programmed instructions provided by a ROM or RAM as is commonly known in the art. The controller 60 may vary the rotational speed of the centrifuge rotor 12 by regulating frequency, current, or voltage of the electricity applied to the motor 14. Alternatively, the rotational speed can be varied by shifting the arrangement of a transmission (not shown), such as by changing gearing to alter a rotational coupling between the motor 14 and rotor 12. The controller 60 may receive input from a rotational speed detector (not shown) to constantly monitor the rotation speed of the rotor.

Accumulated buffy coat components, comprising platelets, some white blood cells, and plasma, are removed via the first collection line 112. As the platelets, plasma, white blood cells, and possibly a small number of red blood cells pass through the first collection line 112, these components flow into the fluid chamber 30, filled with the priming fluid, so that a saturated fluidized particle bed may be formed. The platelets flow toward the first collection line 112. The priming fluid along the inner walls of the separation vessel 28 reduces the effective passageway volume and area in the separation vessel 28 and thereby decreases the amount of blood initially required to prime the system in a separation process. The reduced volume and area also induces higher plasma and platelet velocities next to the stratified layer of red blood cells, in particular, to "scrub" platelets toward the first collection line 112. The rapid conveyance of platelets increases the efficiency of collection.

The fluid chamber 30 is configured to allow cyclic collection of selected particles, such as platelets, followed by efficient evacuation of the cells into a collection bag. In contrast to other chamber designs for forming saturated fluidized beds, the fluid chamber described herein has particular application for the automated collection of blood components in that a bolus of cells having selected characteristics can be collected in the fluid chamber 30 and then flushed with low density fluid into a collection bag and these steps can be repeated multiple times, allowing a larger quantity of the selected cells to be collected from the donor or patient while reducing the amount of time necessary for the donation process. Collection of cells in the fluid chamber can be monitored by the camera 72 and the device controller 60. When a selected quantity of cells have been collected in the fluid chamber 30, the flow of plasma through the chamber can be increased and the collected cells can be washed out of the chamber and directed into a collection bag.

Frame-by-Frame Origin Calibration

In a high-speed centrifuge for separating blood components, control of the interface between blood components presents significant control problems. The present apparatus controls the interface location by measuring light intensity in the collect port monitoring region 204 in the collect port by detecting the presence or absence of RBC's in the collect port, and by monitoring the interface 216 or 218 in the phase boundary or interface monitoring region 202. The light intensity in the collect port can be measured by both an average value over a relatively brief period of time or by a median value over a longer period of time or by a combination of both measurements. The location of the interface is detected by a series of image processing steps, which allow the apparatus to recognize a boundary or interface despite limitations such as the high speed of the centrifuge rotor, the characteristics of stroboscopic light used for observation, or the limits of data processing time. Monitoring the interface in the interface monitoring region 202 allows the apparatus to determine and control the location of the interface reliably. In order for the apparatus to control the interface, a reference position on the disposable blood processing bag, which is carried on the rotor, must be rapidly and reliably determined. In this invention, this is accomplished by a detection algorithm 230, which monitors the L-shaped calibration marker or optical reference 214. The detection algorithm 230 is shown in FIGS. 6a through 6f.

An optically controlled centrifuge for blood separation, as described herein, presents certain problems for the control of the apparatus. With a camera mounted on the frame and observing indistinct phenomena on a rotor spinning in excess of 3000 rpm, vibration is a persistent problem. As viewed through the camera, the image of the separation chamber shakes. Moreover, distances between the camera and observation areas cannot be controlled to the requisite tolerances for observation purposes. This is particularly true where, as herein, the blood is to be processed in a disposable blood separation chamber. Consequently, the location of observation regions must be determined dynamically. In the present invention, an optical reference having at least two non-parallel edges is mounted near the separation chamber. An intersection derived from edges is determined for use as an origin. Observation regions are established with respect to the origin and pixels falling within the observation regions are used to detect phase boundaries and outflow conditions for controlling the blood processing apparatus, as more fully described in U.S. application Ser. No. 11/772,692 and U.S. application Ser. No. 11/774,073. Because of vibration and relative motion between the camera and the separation chamber, it is unlikely that the same pixels in the camera will image the observation regions from one rotation to the next. Nevertheless, by selecting pixels with reference to a dynamically determined origin, a stable view of the observation regions can be obtained.

In the present invention, a series of points representing an edge is measured by collecting raw intensity data from pixels in the camera imaging a region that crosses the edge, filtering the intensity data to reduce variation, and differences between adjacent pixels. There is an abrupt change from light to dark at the edge, which is detected by a difference minima. A set of data points, preferably about five (5), is collected for each edge, and a line is computed through the points. An error measurement, for example, the root mean square error, is calculated for each line. If the error is too large, the image (or "frame") for the current rotation is abandoned. The data is deemed too imprecise or noisy. A new frame would be available in about 40 microseconds, and the process can begin again. The line with the least error is selected as a referent line. A new or dependant line is calculated for the line with the greater error. The dependant line is a mathematical construct created at the known angle between the two edges. This angle may be any acute or obtuse angle less than 180 degrees. The preferred angle is 90 degrees.

The intersection of the two edges is usually physically chamfered. To provide a precise intersection of the referent and dependant lines, they are preferably calculated at an offset from their constituent data points. The intersection of the calculated lines will not fall in the chamfer area and data from the chamfered area will be excluded from calculations. The error function is again computed for the dependant line. If the error exceeds a selected maximum, the frame is discarded, as described above.

Using the parameters of the lines a transformation function is produced, which translates data points from an (r, s) co-ordinate domain derived from measurements of the edges into an (x, y) co-ordinate domain used to identify pixels in the observation areas. To test the transformation, the data points for the two edges are translated from the (r, s) domain into the (x, y) domain and the error function is computed once again. If the error exceeds and maximum error limit, the frame is abandoned.

If the data passes the tests, the pixels falling within the observation regions identified with reference to the origin that has been identified as the intersection of the referent and dependant lines are used determine the position of phase boundaries and out flow characteristics. The process outlined above and described more completely hereafter allows for a frame by frame determination of the location of an origin in the pixel field of the camera and for a determination that the image is sufficiently clear for the collection of data. Vibration and relative motion between the rotor and separation chamber and the camera causes the image detected by the camera to move in the (x, y) plane and to come in and out of focus. The method described allows the apparatus to discard a frame that is too blurry to provide accurate data and to locate a consistent origin from frame to frame.

Figure 7:
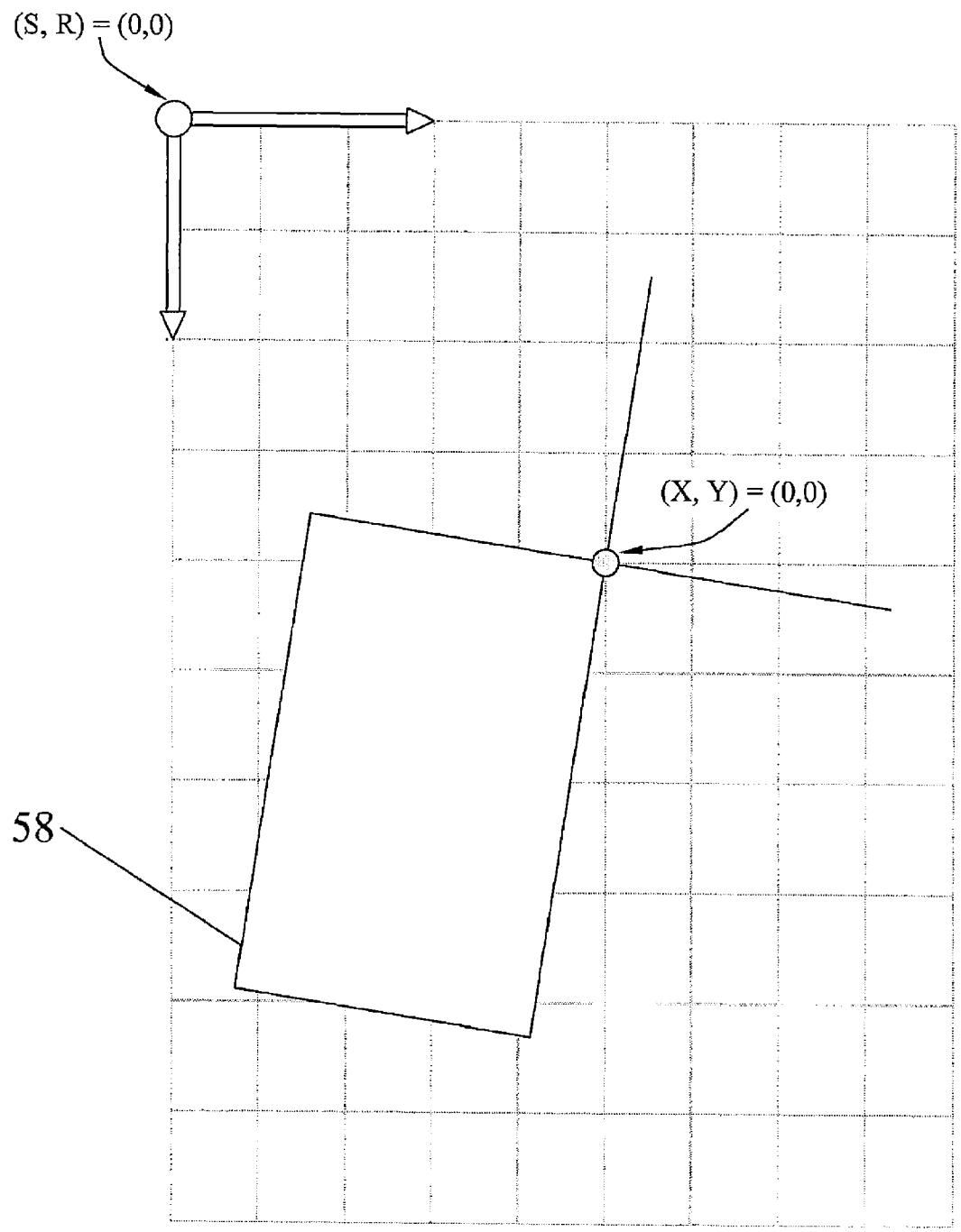
FIG. 7 is a diagram showing the relationship of an (r, s) co-ordinate system and an (x, y) co-ordinate system.

As shown conceptually in FIG. 7, the (r, s) co-ordinate domain is an orthogonal planar reference system in two co-ordinates. Herein, the (r, s) domain is associated with the machined, right-angle reference block 214 shown in FIG. 5. The (x, y) co-ordinate domain is also an orthogonal planar reference system in two co-ordinates. The (x, y) is associated with the phase boundary monitoring region 202 or the collect port monitoring region 204 or both. The origin of the (x, y) domain is usually offset from the origin of the (r, s) domain and the two axis of the two domains are not necessarily parallel to each other. The present invention develops a transformation of information from one domain to the other. The transformation takes the following form, which specifies the conversion between S,R (pixel) coordinates and X,Y (engineering units) coordinates. The matrix is defined as:

$$\begin{pmatrix} X \\ Y \\ 1 \end{pmatrix} = T \begin{pmatrix} S \\ R \\ 1 \end{pmatrix}$$

$$\begin{pmatrix} S \\ R \\ 1 \end{pmatrix} = T^{-1} \begin{pmatrix} X \\ Y \\ 1 \end{pmatrix}$$

$$T = \begin{pmatrix} P_S \cos\alpha & P_R \sin\alpha & -P_S D_S \cos\alpha - P_R D_R \sin\alpha \\ -P_S \sin\alpha & P_R \cos\alpha & P_S D_S \sin\alpha - P_R D_R \cos\alpha \\ 0 & 0 & 1 \end{pmatrix}$$

$$T^{-1} = \begin{pmatrix} \dfrac{\cos\alpha}{P_S} & -\dfrac{\sin\alpha}{P_S} & -D_S \\ \dfrac{\sin\alpha}{P_R} & \dfrac{\cos\alpha}{P_R} & D_R \\ 0 & 0 & 1 \end{pmatrix}$$

Where $P_S$ is the pixel size (in microns) along the S axis, $P_R$ is the pixel size (in microns) along the R axis, a is the angular rotation between the S,R and X,Y coordinate systems, $D_S$ is the S position of the reference corner, and $D_R$ is the R position of the reference corner.

Figure 8:
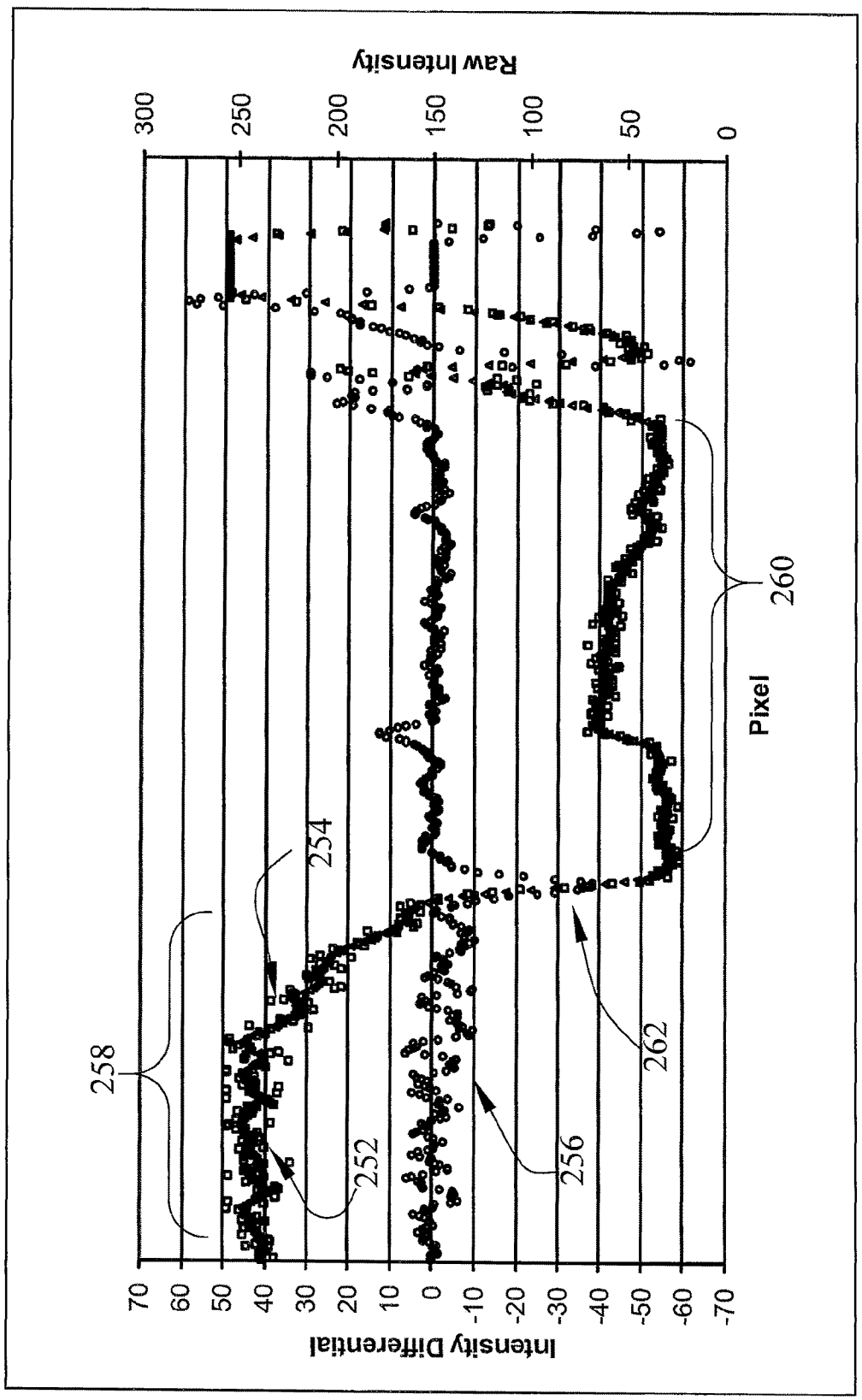
FIG. 8 is a graph of signals for recognizing data points representing an edge of an optical reference.

The optical reference 214 has a horizontal edge 232 and a vertical edge 234. Preferably, these edges 232, 234 intersect at a right angle, although the angle might also be acute or obtuse. The detection algorithm begins 236 by identifying an r Axis Line representative of the horizontal edge 232. An index i is initialized 238. Data points representing detected positions along the edge are added 240 and the index is incremented 242 until a selected number of data points are collected 244. Data points represent transitions from dark to light along the horizontal edge, as determined by the camera. The process of selecting data points is represented graphically in FIG. 8. Raw intensity data 252 acquired from pixels in the field of view of the camera along a line generally parallel to the s axis (that is, radially) for detecting points on the horizontal edge 232 may be filtered 254 to reduce noise related variations. Taking the difference 256 between adjacent pixels, moving from light 258 to dark 260, a minimum (absolute value maximum) difference 262 is found at the pixels closest to the edge 232. A horizontal sweep would be used to locate points on the vertical edge 234. If a satisfactory set of data points is collected, a representative line is fitted 264 through the data points. If the data points are sufficiently close to the line, for example if the mean square fit of the data to the line is less than a predetermined limit, the r Axis Line fit criteria is satisfied 266, and the program can continue. Otherwise, the program is interrupted 268. An interruption in the program implies that the apparatus will attempt to acquire a satisfactory image on the subsequent rotation of the centrifuge.

The program then calculates selected characteristics of the r line. The slope of the line is computed 270. An offset 272 is added to the data. This essentially moves the line representing the horizontal edge 232 upward so that the line does not intersect a chamfer at the junction of the two edges 232, 234. Data points for the vertical edge will be selected in a region above the offset line. Finally, an error co-efficient for the data with respect to the r Axis line is computed. This co-efficient may be, for example, the root mean squared error of the data with respect to the line.

The detection algorithm next identifies an s Axis Line representative of the vertical edge 234. An index i is initialized 276. Data points representing detected positions along the edge are added 278 and the index is incremented 280 until a selected number of data points are collected 282. Data points represent transitions from dark to light along the vertical edge, as described above. If a satisfactory set of data points is collected, a representative line is fitted 284 through the data points. If the data points are sufficiently close to the line, for example if the mean square fit of the data to the line is less than a predetermined limit, the s Axis Line fit criteria is satisfied 286, and the program can continue. Otherwise, the program is interrupted 288.

The program then calculates the selected characteristics of the s Axis line. The slope of the line is computed 290. An offset 292 is added to the data. As before, this moves the line representing the vertical edge 234 sideways so that the line does not intersect the chamfer at the junction of the two edges 232, 234. Finally, an error co-efficient for the data with respect to the s Axis line is computed. This co-efficient may be, for example, the root mean squared error of the data with respect to the s Axis line.

The next major feature of the program selects the line having the most consistent data, that is data that is most linear, and then re-calculates the other line at a right angle (or other angle depending on the optical reference 214) to the selected line. An offset for the calculated line is selected to minimize error of the data points with respect to the calculated line. The error is computed, and, if the error exceeds a pre-determined limit, the program is interrupted in favor of the next frame, as explained above. This feature comprises steps 296 through 360.

In step 296, the program compares the error for the s Axis line to the error for the r Axis line. If the error for the s Axis line is smallest, a line will be calculated for the horizontal or r Axis, representing the horizontal edge 232. The program will calculate an offset for the point where the calculated r Axis will cross the s Axis according to the following formula:

$$a = \frac{\frac{2}{N}\sum s_i - \left(\frac{2}{N}\sum r_i\right)m}{2}$$

where a is the offset, N is the number of data points in the selected line, $s_i$ and $r_i$ are data points along the vertical and horizontal edges 234, 232 respectively, and m is the slope of the horizontal or r Axis line, set, in this example, to −90 degrees from the s Axis line. To calculate the offset a, an index i is set 298 to zero. Position sums ($\Sigma s_i$ and $\Sigma r_i$) for the s Axis 300 and for the r Axis 302 are accumulated for the number of data point along the s Axis and the index i is incremented 304 until the number of points along the s Axis has been reached 306. The respective position sums are multiplied by 2 and divided by the number of data of data points along the r Axis 308 and the s Axis 310, respectively. The r Slope is set 312 to −90 degrees from the s Axis line. This slope is forced to match the known included angle in the optical reference 214, in this case, 90 degrees. Of course, other angles could be used. The offset for the calculated r or horizontal line is calculated 314 as half of the accumulated s Axis values minus the sum of the r Axis values times the r Slope. The sum for the r Axis and an index are cleared 316, 318. The error each data point along the r Axis, that is, the deviation of the point from the calculated and offset r Line, is calculated 320 and the square of each deviation is accumulated 322. The index is incremented 324 until all points have been accumulated 326. The average error for the r Axis points is calculated 328.

On the other hand, if the error for the r Axis line is smallest, a line will be calculated for the vertical or s Axis, representing the vertical edge 234. The program will calculate an offset for the point where the calculated s Axis will cross the r Axis. To calculate the offset, an index i is again set 330 to zero. Position sums ($\Sigma s_i$ and $\Sigma r_i$) for the s Axis 332 and for the r Axis 334 are accumulated for the number of data point along the r Axis and the index i is incremented 336 until the number of points along the r Axis has been reached 338. The respective position sums are multiplied by 2 and divided by the number of data of data points along the r Axis 340 and the s Axis 342, respectively. The s Slope is set 344 to −90 degrees from the r Axis line. The offset for the calculated s or vertical line is calculated 346 as half of the accumulated r Axis values minus the sum of the s Axis values times the s Slope. The sum for the s Axis and an index are cleared 348, 350. The error each data point along the s Axis, that is, the deviation of the point from the calculated and offset s Line, is calculated 352 and the square of each deviation is accumulated 354. The index is incremented 356 until all points have been accumulated 358. The average error for the s Axis points is calculated 360.

Depending on which Axis line was calculated, the average error for either the r Axis or the s Axis is compared 362 to a pre-selected maximum. If successful, the calculated line will be at right angles to the other line and will pass through the data points in such a way that the error is comparatively low. If the error is too large, however, the program interrupts 364 processing and allows the device to try to capture another image on the next rotation of the centrifuge.

If the lines representing the edges 232, 234 have been successfully established, the program is prepared to call a "get Transform" subroutine 366 to relate the (r, s) co-ordinates to the (x, y) coordinates of the observation regions. An acceptable average error and an acceptable maximum error are selected 368. Parameters $P_s$, $P_r$, $D_s$, $D_r$, and the offset "a" are selected 370. The transform preferably takes the form set forth above.

The program then implements the transform against the data collected for the horizontal and vertical edges 232, 234 of the marker 214. An error measurement is generated, (preferably a root-mean square measurement), to check the efficacy of the transformation. First, for the horizontal edge, an index p is set 372 to zero. For each data point along the x axis, the data point is transformed 374 into the (x, y) co-ordinate system. The error in the data is computed and summed together 376. If the error is greater 378 than the preselected limit, the program goes 380 to "BREAK", and once again waits for the next frame to appear. The P-counter is incremented 382 until P equals or exceeds 384 the number of data points on the x axis.

Next, for the vertical edge, the index p is set 386 to zero. For each data point along the y axis, the data point is transformed 388 into the (x, y) co-ordinate system. The error in the data is computed and summed together 390. If the error is greater 392 than the preselected limit, the program goes 394 to "BREAK", and once again waits for the next frame to appear. The P-counter is incremented 396 until P equals or exceeds 398 the number of data points on the y axis.

If the signal processing algorithm described above has successfully located an origin, that is, the intersection of the edges 232, 234, and the data has successfully each of the error tests described, and the algorithm has produced a robust transformation for the frame, the apparatus may begin processing 398 the data in observation regions. A preferred apparatus and method for such signal processing has been described in U.S. patent application Ser. No. 11/772,692 and U.S. patent application Ser. No. 11/774,073, the disclosure of which is incorporated herein. Such processing would allow the apparatus to distinguish phase boundaries in the observation region 202 and to distinguish cell types in the outflow region 204. In response to observed changes in the regions 202, 204, various operating parameters, such as the speed of peristaltic pumps, may be adjusted to control the operating characteristics of the blood processing apparatus.

The optical reference control described herein allows for frame by frame recognition of the location of important control features within a vibrating two-dimensional optical field. Moreover, throughout the process of recognizing the reference point, the quality of the visual image being detected is checked. If the error in the quality of the image exceeds certain limits (for example, when the data points are not sufficiently linear), the frame is abandoned without further processing in favor of the next frame or visual image. Finally, the transformation itself is checked against data associated with optical reference 214 before any attempt is made to process data derived from the observation regions. This assures consistent recognition of the same physical observation regions, despite imaging of those regions on different pixels in the camera. Therefore, sensitive optical recognition techniques can be used with respect to the observation regions, in spite of the vibrations and other optical noise associated with a high speed centrifuge.

It will be apparent to those skilled in the art that various modifications and variations can be made to the structure and methodology of the present invention without departing from the scope or spirit of the invention. Rather, the invention is intended to cover modifications and variations provided they come within the scope of the following claims and their equivalents.

What is claimed is:

1. A method for controlling a centrifuge blood processing system for separating fluid components comprising:
    rotating a separation chamber about a central rotation axis, said separation chamber having an optical reference mounted thereon,
    detecting a plurality of observations from said an observation region with a first detector;
    distinguishing said optical reference,
    establishing a two-dimensional co-ordinate domain with respect to said optical reference,
    and gathering data correlated to said co-ordinate domain from said observations of said observation region as detected by said first detector, and
    controlling fluid flow in said blood processing system in response to said data.

2. The method of claim 1 further comprising rejecting an observation of said separation chamber if an error measurement of said optical reference is not within a pre-selected error limit for said optical reference.

3. A method for controlling a centrifuge blood processing system for separating fluid components comprising:
    rotating a separation chamber about a central rotation axis, said separation chamber having an optical reference mounted thereon,
    detecting a plurality of observations from an observation region with a first detector;
    distinguishing said optical reference,
    establishing reference co-ordinates,
    gathering data from said observations of said observation region as detected by said first detector,
    rejecting an observation of said separation chamber if an error measurement of said optical reference is not within a pre-selected error limit for measurement of said optical reference,
    translating said data from said observation region from a first co-ordinate domain into a second co-ordinate domain, and
    controlling fluid flow in said blood processing system in response to said translated data.

4. The method of claim 3 further comprising rejecting an observation of said separation chamber if translated data representing said optical reference is not within a pre-selected error limit for said translated data.

5. A method for controlling a centrifuge blood processing system for separating fluid components comprising:
    rotating a separation chamber about a central rotation axis, said separation chamber having an optical reference mounted thereon,
    detecting a plurality of observations from an observation region with a first detector;
    distinguishing said optical reference, said optical reference comprising at least two non-parallel sides,
    recognizing a first side represented by a first line, fitting a second line to a second side according to a known angle between said first side and said second side, establishing reference co-ordinates, gathering data from said observations of said observation region as detected by said first detector, and controlling fluid flow in said blood processing system in response to said data.

6. The method of claim 5 further comprising translating said data from said observation region from a first co-ordinate domain into a second co-ordinate domain.

7. The method of claim 6 further comprising rejecting an observation of said separation chamber if translated data representing said optical reference is not within a pre-selected error limit for said translated data.

8. The method of claim 5 further comprising rejecting an observation of said separation chamber if data representing an edge of said optical reference are not within a pre-selected error limit for said edge.

9. The method of claim 8 further comprising computing an error measurement for each of said first and second sides and selecting the side with the least error measurement as a referent line.

10. The method of claim 9 further comprising computing a dependant line for the side with the greater error measurement.

11. The method of claim 10 further comprising computing an error measurement for the dependant line and rejecting an observation of said separation chamber if the error measurement for the dependant line is not within a pre-selected error limit for the dependant line.

12. The method of claim 5 wherein the first and second sides are orthogonal to each other.

13. The method of claim 12 further comprising rejecting an observation of said separation chamber if data representing an edge of said optical reference are not within a pre-selected error limit for the edge.

14. The method of claim 13 further comprising computing an error measurement for each of said first and second sides and selecting the side with the least error measurement as a referent line.

15. The method of claim 14 further comprising computing a dependant line for the side with the greater error measurement.

16. The method of claim 15 further comprising computing an error measurement for the dependant line and rejecting an observation of said separation chamber if the error measurement for the dependant line is not within a pre-selected error limit for the dependant line.

17. The method of claim 16 further comprising translating said data from said observation region from a first co-ordinate domain into a second co-ordinate domain.

18. The method of claim 17 further comprising rejecting an observation of said separation chamber if translated data representing said optical reference is not within a pre-selected error limit for said translated data.

* * * * *